United States Patent [19]

Slack et al.

[11] Patent Number: 4,810,820

[45] Date of Patent: Mar. 7, 1989

[54] PROCESS FOR THE PRODUCTION OF POLYISOCYANATES CONTAINING ALLOPHANATE GROUPS

[75] Inventors: William E. Slack, Moundsville; Terry A. Potter; Kenneth L. Dunlap, both of New Martinsville, all of W. Va.

[73] Assignee: Mobay Corporation, Pittsburgh, Pa.

[21] Appl. No.: 84,546

[22] Filed: Aug. 12, 1987

[51] Int. Cl.$^4$ ............................................. C07C 127/22
[52] U.S. Cl. ........................................ 560/27; 560/25; 560/26; 560/115; 560/158; 560/159
[58] Field of Search .................... 560/25, 27, 159, 158, 560/115, 26

[56] References Cited

U.S. PATENT DOCUMENTS

| | | | |
|---|---|---|---|
| 2,784,163 | 3/1957 | Reynolds | 560/158 |
| 2,947,714 | 8/1960 | Leclercq | 560/158 |
| 3,644,490 | 2/1972 | Schmelzer | 560/115 |
| 3,769,318 | 10/1973 | Windemuth et al. | 260/471 |
| 4,152,350 | 5/1979 | Mohring | 560/115 |
| 4,160,080 | 7/1979 | Koenig et al. | 528/59 |
| 4,177,342 | 12/1979 | Bock et al. | 528/45 |
| 4,695,645 | 9/1987 | Merger | 560/158 |

FOREIGN PATENT DOCUMENTS 994890 6/1965 United Kingdom .

OTHER PUBLICATIONS

Ault, "Techniques and Experiments for Organic Chemistry," 4th Ed, pp. 294–296 (1983).
Perry, "Chemical Engineers' Handbook," 5th Ed, 4-20 to 4-29 (1973).

*Primary Examiner*—Michael L. Shippen
*Attorney, Agent, or Firm*—Gene Harsh; Joseph C. Gil; Richard E. L. Henderson

[57] ABSTRACT

Aliphatic and/or cycloaliphatic polyisocyanates containing allophanate groups are produced by reacting (a) a di- and/or polyisocyanate with aliphatic and/or cycloaliphatic isocyanate groups with (b) a hydroxy compound at a temperature of at least 150° C. for no more than 90 minutes and then rapidly cooling the reaction mixture to a temperature of less than 100° C. It is preferred that the reaction be carried out in the absence of oxygen. The products thus obtained are virtually colorless, have a relatively low viscosity and excellent storage stability.

7 Claims, No Drawings

PROCESS FOR THE PRODUCTION OF POLYISOCYANATES CONTAINING ALLOPHANATE GROUPS

BACKGROUND OF THE INVENTION

The present invention relates to a process for the production of aliphatic and/or cycloaliphatic polyisocyanates containing allophanate groups.

Processes for the production of polyisocyanates containing allophanate groups are known. Such processes are disclosed, for example, in U.S. Pat. Nos. 4,177,342, 4,160,080 and 3,769,318 and British Pat. No. 994,890.

British Pat. No. 994,890 discloses a process for the production of polyisocyanates containing allophanate groups in which a urethane isocyanate is reacted with an excess of another diisocyanate. This reaction which may be carried out in the presence of specified catalysts is allowed to continue until the isocyanate content is reduced to that theoretically obtained when complete reaction of the urethane groups is achieved. The products obtained by this process are not however limited to the desired allophanates. Substantial amounts of dimerization and trimerization products are also present particularly where a catalyst has been used. Further, the long reaction times at elevated temperatures required in this disclosed process (at least 24 hours) where no catalyst is used result in discoloration of the final product.

This problem of preparing allophanate polyisocyanates which are not contaminated with dimeric and trimeric polyisocyanates was addressed in U.S. Pat. No. 3,769,318. According to U.S. Pat. No. 3,769,318 allophanates containing at least one aromatically bound isocyanate group are produced by reacting an N-substituted carbamic acid ester with an isocyanate in the presence of a dialkyl ester of sulfuric acid. This reaction is carried out at temperatures of from 20° to 180° C. for 2 to 50 hours. This processiis not, however, suitable for the preparation of allophanate polyisocyanates having aliphatically and/or cycloaliphatically bound isocyanate groups.

U.S. Pat. No. 4,160,080 discloses a process for producing allophanates containing aliphatically and/or cycloaliphatically bound isocyanate groups in which compounds containing urethane groups are reacted with polyisocyanates having aliphatic and/or cycloaliphatic isocyanate groups in the presence of a strong acid. This process is generally carried out at a temperature of from 90° to 140° C. for from 4 to almost 20 hours. Such reaction times are a substantial improvement over the process of British 994,890. However, discoloration of the final product due to exposure to higher temperatures for such prolonged periods is still a problem.

U.S. Pat. No. 4,177,342 discloses a process for the production of polyisocyanates containing allophanate groups in which an organic polyisocyanate is reacted with a hydroxyl carbamate compound. The allophanate is formed at a temperature of from 100° to 180° C. Appropriate reaction times are described as being from 20 minutes to 4 hours. However, it is clear from the examples that a temperature greater than 150° C. was not actually employed. The products of the process are viscous, colorless to yellow polyisocyanates which are liquid or solid hard resins at room temperature.

SUMMARY OF THE INVENTION

It is an object of the present invention to provide a process for the production of polyisocyanates containing allophanate groups which have aliphatically and/or cycloaliphatically bound isocyanate groups (hereinafter "allophanate polyisocyanates") and are virtually free of dimeric isocyanates.

It is also an object of the present invention to provide a process for the production of allophanate polyisocyanates which are substantially colorless and have a relaiively low viscosity.

It is a further object of the present invention to provide a process for the production of allophanate polyisocyanates in which the conversion of isocyanate to allophanate in a given reaction time is substantially greater than that of known processes.

It is also an object of the present invention to provide a process for the production of allophanate polyisocyanates in which no catalyst is required.

It is another object of the present invention to provide allophanate polyisocyanates which are virtually free of dimeric isocyanates, substantially colorless and which have a relatively low viscosity.

These and other objects which will be apparent to those skilled in the art are accomplished by reacting (a) an organic di- and/or polyisocyanate which contains aliphatically and/or cycloaliphatically bound isocyanate groups with (b) an organic compound containing at least one hydroxy group which compound is otherwise inert with respect to isocyanate groups at a temperature of at least 150° C. for a period of from 15 secs to 90 minutes which reaction is preferably carried out in the absence of oxygen. The resultant product is rapidly (i.e., usually within 10 minutes) cooled to a temperature of less than 100° C.

DETAILED DESCRIPTION OF THE INVENTION

The present invention is directed to improved allophanate polyisocyanates and to a process for their production. In the practice of this invention, an isocyanate containing aliphatic and/or cycloaliphatic isocyanate groups is reacted with an organic hydroxyl group containing compound preferably in the absence of oxygen at a temperature of at least 150° C. for up to 90 minutes.

The isocyanate starting materials useful in the present invention include those isocyanates corresponding to the formula

in which
R represents an aliphatic hydrocarbon group with from 2 to 20 (preferably 6–10) carbon atoms, a cycloaliphatic hydrocarbon group having from 4 to 20 (preferably 6-15) carbon atoms or a xylylene group and x represents a number of from 2 to 4, preferably 2.

Specific examples of such isocyanates include: ethylene diisocyanate: tetramethylene diisocyanate; hexamethylene diisocyanate: undecamethylene diisocyanate: 2,4,4-trimethyl-1,6-diisocyanatohexane: isocyanatomethyl-3,5,5-trimethyl-cyclohexylisocyanate: 1,3-diisocyanatocyclobutane: 1,4-diisocyanatocyclohexane; 4,4'-diisocyanato-dicyclohexylmethane: 1,2-bis-(isocyanatomethyl)cyclobutane: trimethylhexane-1,6-disocyanate: 1,11-diisocyanato-undecane: 3- isocyanatomethyl-3,5,5-trimethylcyclohexyl isocyanate: 4,4'-cyclohexane diisocyanate: 4,4'-dicyclohexylmethane-diisocyanate: 1,2-bis-(isocyanatomethyl)-cyclobutane: bisisocyanatomethyl-norbornane (isomeric mixture): 3(4), 8(9)-diisocyanatomethyl-tricyclo(5,2,1,2,6)-decane, p-xylylene diisocyanate, 1,12-dodecane diisocyanate, lysine diisocyanate ($C_1$–$C_8$-alkyl esters), 1,3-diisocyanatocyclo-hexane and 1-isocyanato-3,3,5-trimethyl-5-isocyanato methyl cyclohexane (isophorone diisocyanate). Hexamethylene diisocyanate is preferred.

These isocyanates may be used directly or they may be preliminarily reacted with a hydroxyl compound to form urethane-containing isocyanates. From 0 to 100% of the hydroxyl groups of the hydroxyl compound may be prereacted with a portion of the isocyanate groups present in the isocyanate to form urethane groups prior to the allophanate-forming reaction of the present invention.

Higher than difunctional aliphatic and/or cycloaliphatic polyisocyanates may also be used as part or all of the isocyanate component. Examples of such polyisocyanates include the trimerization products of hexamethylene diisocyanate and of 3-isocyanatomethyl-3,5,5-trimethyl cyclohexylisocyanate which contains isocyanurate groups.

Mixtures of any of the above-identified isocyanates may, of course, also be used.

Hydroxyl compounds useful as starting materials in the process of the present invention include any of the known organic compounds containing at least one hydroxyl group in which no other groups (i.e., other than the hydroxyl group(s)) reactive with isocyanate groups are present. Such compounds include compounds with alcoholic hydroxyl groups and/or phenolic hydroxyl groups. Compounds containing alcoholic hydroxyl groups are however preferred.

Examples of the types of compounds containing alcoholic hydroxyl groups suitable for hhe process of the present invention include low molecular weight mono-hydric to tetrahydric aliphatic alcohols having a molecular weight of from about 32 to 250 which may contain ether bridges: cycloaliphatic monovalent to tetravalent alcohols with molecular weights of from about 88 to 250: araliphatic monohydric to tetrahydric alcohols with molecular weights of from about 103 to 300: and polythioethers, polyacetals, polycarbonates, polyesters and polyethers of the type known to those skilled in polyurethane chemistry having an average molecular weight of from about 250 to 5000, preferably from about 300 to 2000.

Specific examples of suitable organic compounds containing alcoholic hydroxyl groups include: methanol; ethanol; propanol; isopropanol; isomeric butanols: allyl alcohol; pentanols, hexanols and heptanols; 2-ethylhexanol; fatty alcohols having 10 to 20 carbon atoms; ethanediol; (1,2)- and (1,3)-propane diol; (1,2) and (1,3)-butanediol and (1,4)- and (1,5)-pentanediol; neopentyl glycol; (1,6)- and (2,5)-hexane diol; 3-methyl-pentane-diol-(1,5); 2-methyl-2-propylpropanediol-(1,3); 2,2-diethyl-propanediol-(1,3); 2-ethylhexanediol-(1,3): 2,2,4-trimethylpentanediol-(1,3); trimethylhexane-diol-(1,6); decanediol-(1,10); dodecanediol-(1,2); 2-butanediol-(1,4); 2-methylene-propanediol-(1,3); glycerol; butanetriol; 2-hydroxymethyl-2-methylpropane diol-(1,3); 1,2,6-hexanetriol; trimethylolethane; trimethylolpropane; pentaerythritol; ethyleneglycol monoalkyl- or monoaryl-ether; propyleneglycol monoalkyl ether; diethyleneglycol; triethyleneglycol; tetraethyleneglycol; cyclopentanol; cyclohexanol; methylcyclohexanol; trimethylcyclohexanol; 4-tertiarybutylcyclohexanol; menthol; borneol and isoborneol; 2-hydroxdecaline; 1,2-; 1,3- and 1,4-cyclohexanediol; 2,4-dihydroxy-1,1,3,3-tetramethylcyclobutane; 1,4-bishydroxymethyl-cyclohexane; bis-(4-hydroxycyclohexyl)methane; 2,2-bis-(4-hydroxycyclohexyl)-propane; 2-methyl-2,4-bis-(4-hydroxycyclohexyl)-pentane; furfuryl- and tetrahydrofurfuryl-alcohol; bis-hydroxymethyl-norbornane: dihydroxymethyl-tricyclododecane; benzyl alcohol; phenylethyl alcohol; 3-phenylpropanol and 4,4'-di-(2-hydroxyethyl)-diphenylmethane.

Suitable polyesters with hydroxyl groups include the reaction products of polyhydric, preferably dihydric alcohols to which trihydric alcohols may be added with polybasic, preferably dibasic carboxylic acids. Instead of free polycarboxylic acids, the corresponding polycarboxylic acid anhydrides or the corresponding polycarboxylic acid esters of lower alcohols or mixtures thereof may be use for preparing the polyesters. The polycarboxylic acids may be aliphatic, cycloaliphatic, aromatic and/or heterocyclic and they may be substituted, e.g. by halogen atoms, and/or unsaturated. Examples of appropriate acids include: succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimeric and trimeric fatty acids such as oleic acid which may be mixed with monomeric fatty acids, dimethyl terephthalate and terephthalic acid-bis-glycol esters. Examples of suitable polyhydric alcohols include: ethylene glycol, (1,2)- and (1,3)- propylene glycol, (1,4)- and (2,3)-butylene glycol, (1,6)-hexane diol, (1,8)-octanediol, neopentylglycol, cyclohexanedimethanol (1,4-bis-hydroxymethylcyclohexane), 2-methyl-1,3-propanediol, glycerol, trimethylolpropane, (1,2,6)-hexanetriol, trimethylolethane, pentaerythritol, quinitol, mannitol and sorbitol, methylglycoside, diethylene glycol, triethylene glycol, tetraethylene glycol, polyethylene glycols, dipropylen glycol, polypropylene glycols, dibutylene glycol and polybutylene glycols. Polyesters of lactones such as $\epsilon$-caprolactone or hydroxycarboxylic acids such as $\omega$-hydroxycaproic acid may also be used.

The polyethers useful in the present invention which have from one to four hydroxyl groups are also known and may be prepared, for example, by the polymerization of epoxides such as ethylene oxide, propylene oxide, butylene oxide, tetrahydrofuran, styrene oxide or epichlorohydrin, either each on its own, e.g., in the presence of boron trifluoride, or by addition of these epoxides, either as mixtures or successively, to starting components having reactive hydrogen atoms. Suitable starting components include water, alcohols and phenols, e.g., ethylene glycol, (1,3)- and (1,2)-propylene glycol, trimethylolpropane and 4,4'-dihydroxydiphenylpropane.

Among the polythioethers useful in this invention are the condensation products obtained by reacting thiodiglycol on its own and/or with other glycols, dicarboxylic acids or formaldehyde. The products obtained are polythio mixed ethers, polythio ether esters or polythio ether polyacetals, depending upon the co-components.

Suitable polyacetals include, for example, the compounds which can be prepared from glycols such as diethylene glycol, triethylene glycol, 4,4'-dioxethoxydiphenyl dimethylmethane, hexanediol and formaldehyde. Suitable polyacetals for the purpose of the invention may also be prepared by the polymerization of cyclic acetals.

The polycarbonates with hydroxyl groups used are known and include those which can be prepared by the reaction of diols such as (1,3)-propanediol, (1,4)-butanediol and/or (1,6)-hexanediol, diethylene glycol, triethylene glycol or tetraethylene glycol with diarylcarbonates, e.g., with diphenylcarbonate or phosgene.

Simple aliphatic alcohols, polyester polyols and polyether polyols are preferred for the process according to the invention.

Mixtures of the hydroxyl compounds mentioned above may, of course, be used. This is in fact a preferred embodiment of the process according to the invention since, by using a mixture of hydroxyl compounds differing in their functionality, the functionality of the allophanate-polyisocyanate obtained may be adjusted as desired.

It is important that any hydroxyl compound employed in the process of the present invention be free of any base which may have been present during its preparation. Such a base would promote the unwanted formation of trimers.

No other additives such as catalysts or acids are required in the practice of the present invention. However, if an isocyanate is preliminarily converted to a urethane-containin material, it may be advantageous to include any of the known urethane catalssts in the mixture of isocyanate and hydroxyl group-containing material until the desired degree of urethane formation has been reached. The catalysts may then be removed from the reaction mixture prior to allophanate formation but such removal is not required.

When carrying out the process of the present invention, the reactants are generally used in quantities such that from 3 to 20 equivalents of NCO groups are present for each equivalent of hydroxyl groups, preferably 8 to 15 equivalents of NCO groups per equivalent of hydroxyl groups. If a compound containing urethane groups is preliminarily formed from the isocyanate, an appropriate excess of isocyanate component, preferably diisocyanate component is used.

The reaction in accordance with the present invention is carried out at a temperature of at least 150° C., preferably at least 200° C. and most preferably at least 250° C. This reaction is generally carried out for a period of from 15 seconds to 1.5 hours, preferably from 15 seconds to 30 minutes and most preferably from 1 to 15 minutes. Generally, the higher the reaction temperature, the shorter the reaction time necessary. For example, at 250° C. the reaction time may be as short as 15 seconds whereas at 150° C. a reaction time of 1½ hours may be necessary.

It is preferred that the allophanate-forming reaction be carried out in the absence of oxygen because the product thus-formed is substantially improved with respect to color. In fact, despite the high reaction temperature employed, the product allophanates are substantially colorless when formed in the absence of oxygen.

When the allophanate-forming reaction has been completed, the reaction mixture is quickly cooled to a temperature below 100° C., preferably to less than 70° C., most preferably to approximately 25° C. This cooling is carried out in a period of no more than 10 minutes, preferably less than five minutes.

In the practice of the present invention, the isocyanate (preferably a diisocyanate) is introduced into the reaction vessel and the hydroxyl compound which is at a temperature of at least 25° C. is added thereto. Appropriate reaction vessels are known in the art. It is preferred, however, that a hot tube plug flow reactor such as that used in Examples 3 and 6 be employed.

If the same isocyanate is to be converted to a urethane containing isocyanate before being converted to the allophanate, it is simplest to introduce excess isocyanate from the start. In such cases, the isocyanate is advantageously used in a quantity such that the NCO-/OH ratio is in the range of from approximately 3:1 to 12:1.

When carrying out the process according to the invention, the nature and quantitative proportions of the starting materials are generally chosen so that allophanates containing at least two isocyanate groups, (i.e., allophanate polyisocyanates) are obtained as products of the process. These products according to the invention are distinguished by their excellent stability during thin layer treatment even at temperatures of above 180° C. or more. The side reactions and equilibration reactions which are observed in the case of polyisocyanates with a biuret structure and and an increase in viscosity do not occur.

The process according to the invention may suitably be carried out continuously or on a batch basis. In a continuous process, several reactors may be arranged one behind the other in hhe form of cascade. Diisocyanate, hydroxyl compound and any optional additives (e.g., a catalyst) are fed continuously into the first reactor. The temperature and rate of input are adjusted so that the reaction is completed by the time the reaction mixture leaves the last reactor. The crude product is then passed through a thin layer evaporator where it is freed from excess diisocyanate and then returned to the first reactor.

The allophanate polyisocyanates prepared according to the invention may be used for the production of polyurethane foams, elastomers, coatings and adhesives after removal of excess diisocyanate.

They are particularly suitable raw materials for the production of high quality, lightfast and weather resistant lacquers, and may be used in combination with hydroxyl functional higher molecular weight compounds. The allophanate polyisocyanates prepared according to this invention can be combined with polyeseer or acrylic polyols to form lacquers with excellent hardness and improved flexibility as compared to, for example, lacquers based on polyisocyanates containing the biuret or isocyanurate structures.

Another advantage of the process according to the invention lies in the wide range of possible variations, particularly with regard to the nature and proportions of inexpensive starting materials (hydroxyl-containing compounds). For example, the isocyanate cyanate functionality of the products obtained by the process according to the invention can be controlled within wide limits by suitable choice of the hydroxyl compound. The use of fatty alcohols gives rise to products which are readily soluble in petroleum hydrocarbons. Very hard lacquers are obtained by using cycloaliphatic or aromatic hydroxyl compounds.

The invention is further illustrated but is not intended to be limited by the following examples in which all parts and percentages are by weight unless otherwise specified.

Examples

EXAMPLE 1

To a 250 ml three-necked flask equipped with a mechanical stirrer and condenser was added 100 g hexamethylene diisocyanate. 8.8 g of n-butanol were then added at 25° C. with stirring. The temperature was raised to 70° C. and after 2 hours the isocyanate content of the reaction mixture was 41.4%, which corresponds to complete conversion of the hydroxyl groups to urethane groups. The reaction mixture was then heated over a 5 minute period to 250° C., held for 1 minute, then cooled to less than 70° C. over a 4 minute period. The resulting clear liquid had an isocyanate content of 37.8%, which corresponds to a 78% conversion of the urethane groups to allophanate groups. Unreacted hexamethylene diisocyanate was removed by thin layer distillation to afford a liquid product with a viscosity of 99 mPa.s/25° C. and an isocyanate content of 17.3%. The product contained 0.5% unreacted hexamethylene diisocyanate.

The composition of the product was found by both gel chromatography and IR analysis to contain allophanate and urethane groups and the dimer and trimer of hexamethylene diisocyanate. This is very similar to material prepared at 110° C. using the traditional allophanate catalyst, zinc acetylacetonate (Example 2).

EXAMPLE 2

To a 1000 ml three-necked flask equipped with a mechanical stirrer and condenser was added with stirring 840 g hexamethylene diisocyanate, 73.8 g n-butanol and 0.13 g zinc acetylacetonate. The temperature was raised to 110° C., held for 1.5 hours, then cooled to 25° C. over a 10 minute period. The resulting clear liquid had an isocyanate content of 37.5%, which corresponds to a 84.8% conversion to allophanate groups. Unreacted hexamethylene diisocyanate was removed by thin layer distillation to afford a liquid product with a viscosity of 121 mPa.s/25° C. and an isocyanate content of 17.9%. The product contained 0.1% unreacted hexamethylene diisocyanate.

The composition of this product was found to be very similar to the material obtained in Example 1.

EXAMPLE 3

To a feed tank was added a mixture of hexamethylene diisocyanate and n-butanol having weight ratio of 11.36 to 1. This material was then pumped, without preliminary conversion to the urethane through a hot tube reactor at 235° C. in which the heat-up from 25° C. to 235° C. required 4 minutes. The reactor was maintained at 235° C. for 12 minutes then cooled over an 8 minute period to 25° C. The isocyanate content of the resulting reaction mixture was 37.9%, which corresponds to 76% conversion of the urethane groups to allophanate groups. Unreacted hexamethylene diisocyanate was removed by thin layer distillation to afford a liquid product with a viscosity of 106 mPa.s/25° C. and an isocyanate content of 16.9%. The product contained 0.4% unreacted hexamethylene diisocyanate.

EXAMPLE 4

Following the procedure described in Example 1, 100 parts of hexamethylene diisocyanate and 6 parts neopentyl glycol (NPG) were converted to the urethane at 70° C. (42.6% NCO). The reaction mixture was then heated over a 5 minute period to 250° C., held for 2 minutes, then cooled to less than 70° C. over a 3 minute period. The resulting liquid had an isocyanate content of 39.4%, which corresponds to a 70% conversion of the urethane groups to allophanate groups. Unreacted hexamethylene diisocyanate was removed by thin layer distillation to afford a liquid product with a viscosity of 4250 mPa.s/25° C. and an isocyanate content of 18.5%. The product contained 0.5% unreacted hexamethylene diisocyanate.

EXAMPLE 5

To a 5-liter three-necked flask equipped with a mechanical stirrer and condenser was added with stirring 3000 parts hexamethylene diisocyanate and 180 parts neopentyl glycol (NPG). The reaction mixture was heated to 87° C. 0.4 parts zinc acetylacetonate were added. Heating was continued until the reaction mixture had reached 99° C., which required 10 minutes. 0.5 parts benzoyl chloride were added, the reaction mixture held for an additional 12 minutes at 99° C. then cooled to 25° C. over a 30 minute period. The resulting clear liquid had an isocyanate content of 39.3%, which corresponds to a 72% conversion to allophanate groups. Unreacted hexamethylene diisocyanate was removed by thin layer distillation to afford a liquid product with a viscosity of 6450 mPa.s/25° C. and an isocyanate content of 18.5%. The product contained 0.2% unreacted hexamethylene diisocyanate.

The composition of this product was found to be very similar to the material obtained in Example 4.

EXAMPLE 6

To a feed tank was added a mixture of 100 parts hexamethylene diisocyanate and 6 parts neopentyl glycol (NPG) which had been preliminarily converted to the corresponding urethane at 70° C. (42.8% NCO). This mtterial was then pumped, at 25° C. through a hot tube plug flow reactor at 270° C. The heat-up from 25° C. to 270° C. required 1.5 minutes. The reaction mixture was maintained at 270° C. for 4 minutes and then cooled over a 2.7 minute period to 25° C. The isocyanate content of the resulting reaction mixture was 39.5%, which corresponds to 67.4% conversion of the urethane groups to allophanate groups. Unreacted hexamethylene diisocyanate was removed by thin layer distillation to afford a liquid product with a viscosity of 4140 mPa.s/25° C. and an isocyanate cnntent of 18.1%. The product contained 0.8% unreacted hexamethylene diisocyanate.

EXAMPLE 7

To a 250 ml three-necked flask equipped with a mechanical stirrer and condenser was added 100 g hexamethylene diisocyanate. To this at 25° C. was added, with stirring, 5.4 g of 1,3-butanediol. The reaction mixture was then heated over a 4 minute period to 250° C., held for 2 minutes, then cooled to less than 70° C. over a 5 minute period. The resulting clear liquid had an isocyanate content of 37.9%, which corresponds to a 102% conversion to the allophanate.

EXAMPLE 8-18

Following the same procedure as was used in Example 1, a urethane-containing isocyanate material was preliminarily formed from the materials identified in Table 1 and then converted on a batch-basis to the corresponding allophanate under the specified reaction conditions. The allophanate was stripped of excess hexamethylene diisocyanate (HX) unless otherwise indicated.

TABLE I

| Ex. | Formulation | Heat-up Time (min) | Reaction Time (min) | Reaction Temp. °C. | Cool-Down Time (min) | % NCO Reaction Mixture | % Conversion to Allophanates (Based on NCO Drop) | % NCO Final Product | Visc. at 25° C. (mPa.s) Final Product | % by weight Free Hexamethylene Diisocyanate | APHA Color |
|---|---|---|---|---|---|---|---|---|---|---|---|
| 8 | 100 parts HX<br>3.5 parts 2,5-hexanediol<br>4.4 parts 2-butanol | 5 | 2.5 | 250 | 6 | 37.5 | 91 | 17.9 | 768 | 0.7 | — |
| 9 | 100 parts HX<br>7 parts 2,5-hexanediol | 5 | 1.5 | 250 | 6 | 38.3 | 81 | 18.0 | 4320 | 0.5 | — |
| 10* | 5.5 parts ethanol<br>100 parts HX | 5 | 2 | 250 | 6 | 39.5 | 66 | — | — | — | — |
| 11* | 3.8 parts methanol<br>100 parts HX | 5 | 2 | 250 | 6 | 41.1 | 48 | — | — | — | — |
| 12* | 7.1 parts 2-propanol<br>100 parts HX | 5 | 2 | 250 | 6 | 39.1 | 63 | — | — | — | — |
| 13* | 8.8 parts 2-butanol<br>100 parts HX | 5 | 2 | 250 | 6 | 38.0 | 74 | — | — | — | — |
| 14 | 6 parts NPG<br>100 parts HX | 6 | 4 | 250 | 5 | 37.9 | 102 | 18.3 | 6040 | 0.4 | 90 |
| 15 | 34.9 parts 2-pentanol<br>100 parts HX | 8 | 8 | 250 | 8 | 14.5 | 83 | 9.1 | 4490 | 0.4 | 75 |
| 16 | 29 parts 2-butanol<br>100 parts HX | 8 | 15 | 250 | 8 | 17.7 | 66 | 10.8 | 11460 | 0.8 | 50 |
| 17 | 6 parts NPG<br>34.9 parts 2-pentanol<br>200 parts HX | 8 | 5 | 250 | 8 | 26.0 | 74 | 14.4 | 2090 | 0.5 | 80 |
| 18 | 6 parts NPG<br>34.9 parts 2-pentanol<br>200 parts HX | 8 | 8.2 | 250 | 8 | 23.7 | 100 | 13.9 | 7060 | 0.7 | 85 |

*Run as Example 1 but not stripped of excess HX.

EXAMPLES 19-26

Following the procedure used in Example 6, a urethane-containing material was preliminarily formed from the materials identified in Table 2. This material was then converted to an allophanate in a hot tube plug flow reactor under the specified conditions and the product allophanate stripped of excess hexamethylene diisocyanate (HX).

TABLE II

| Ex. | Formulation | Heat-up Time (min) | Reaction Time (min) | Reaction Temp. °C. | Cool-Down Time (min) | % NCO Reaction Mixture | % Conversion to Allophanates (Based on NCO Drops) | % NCO Final Product | Visc. at 25° C. (mPa.s) Final Product | % by weight Free Hexamethylene Diisocyanate | APHA Color |
|---|---|---|---|---|---|---|---|---|---|---|---|
| 19 | 100 parts HX<br>3.9 parts NPG<br>3 parts n-butanol | 2 | 5 | 265 | 3.6 | 38.0 | 93 | 17.8 | 872 | 0.8 | 70 |
| 20 | 100 parts HX<br>4.5 parts NPG<br>6.4 parts n-butanol | 1.4 | 1.6 | 250 | 1.5 | 36.0 | 39 | 16.9 | 830 | 0.4 | |
| 21 | 100 parts HX<br>6 parts NPG | 1.2 | 1.4 | 260 | 1.3 | 40.3 | 50 | 18.3 | 3390 | 0.6 | — |
| 22 | 100 parts HX<br>9 parts NPG | 1.4 | 1.6 | 275 | 1.5 | 35.9 | 49 | 17.5 | 8900 | 0.7 | — |
| 23 | 100 parts HX<br>5 parts TMP | 1.4 | 1.6 | 260 | 1.5 | 40.8 | 52 | 18.8 | 44800 | 0.4 | — |
| 24 | 100 parts HX<br>2.5 parts TMP<br>4.1 parts n-butanol | 1.4 | 1.6 | 255 | 1.5 | 40.3 | 50 | 18.6 | 1240 | 0.3 | — |
| 25 | 100 parts HX<br>6 parts NPG | 1.4 | 4 | 265 | 2.7 | 39.4 | 70 | 18.0 | 5100 | 0.7 | 1 |
| 26 | 100 parts HX<br>3.9 parts NPG<br>3 parts n-butanol | 2 | 5 | 265 | 3.6 | 38.2 | 87 | 18.0 | 1050 | 0.8 | 112 |

EXAMPLES 27-68

Following the procedure used in Example 7, a solution made from the materials identified in Table 3 was converted to an allophanate in a batch reactor under the specified reaction conditions.

TABLE III

| Ex. | Formulation | Heat-up Time (min) | Reaction Time (min) | Reaction Temp. °C. | Cool-Down Time (min) | % NCO Reaction Mixture | % Conversion to Allophanates (Based on NCO Drops) |
|---|---|---|---|---|---|---|---|
| 27 | 7.5 parts 1,4 butanediol<br>140 parts HX | 4 | 2 | 250 | 6 | 39.8 | 62 |
| 28 | 7.5 parts 1,4 butanediol<br>140 parts HX | 4 | 4 | 250 | 6 | 38.3 | 94 |
| 29 | 12.1 parts 2,2,4-trimethyl pentane diol<br>140 parts HX | 4 | 2 | 250 | 6 | 38.0 | 76 |
| 30 | 12.1 parts 2,2,4-trimethyl pentane diol<br>140 parts HX | 4 | 4 | 250 | 6 | 37.7 | 82 |
| 31 | 12.3 parts 2-butanol<br>140 parts HX | 5 | 2 | 250 | 6 | 38.0 | 74 |
| 32 | 12.3 parts 2-butanol<br>140 parts HX | 5 | 4 | 250 | 6 | 37.6 | 83 |
| 33 | 7.5 parts 2,3-butanediol<br>140 parts HX | 4 | 2 | 250 | 6 | 38.5 | 89 |
| 34 | 7.5 parts 2,3-butanediol<br>140 parts HX | 4 | 4 | 250 | 6 | 38.1 | 98 |
| 35 | 13.3 parts 2-ethyl-2-butyl 1,3-propane diol<br>140 parts HX | 4 | 2 | 250 | 6 | 37.7 | 76 |
| 36 | 13.3 parts 2-ethyl-2-butyl-1,3-propane diol<br>140 parts HX | 4 | 4 | 250 | 6 | 36.6 | 100 |
| 37 | 6.3 parts 1,2-propanediol<br>140 parts HX | 4 | 2 | 250 | 6 | 34.1 | 188 |
| 38 | 6.3 parts 1,2-propanediol<br>140 parts HX | 4 | 4 | 250 | 6 | 31.7 | 238 |
| 39 | 6.3 parts 1,3-propanediol<br>140 parts HX | 4 | 2 | 250 | 6 | 39.7 | 71 |
| 40 | 6.3 parts 1,3-propanediol<br>140 parts HX | 4 | 4 | 250 | 6 | 37.9 | 108 |
| 41 | 8.7 parts NPG<br>140 parts HX | 4 | 2 | 250 | 6 | 38.6 | 79 |
| 42 | 8.7 parts NPG<br>140 parts HX | 4 | 4 | 250 | 6 | 38.0 | 92 |
| 43 | 8.7 parts 1,5-pentanediol<br>140 parts HX | 4 | 2 | 250 | 6 | 38.5 | 81 |
| 44 | 9.8 parts 2,5-hexanediol<br>140 parts HX | 4 | 2 | 250 | 6 | 38.2 | 83 |
| 45 | 9.8 parts 2,5-hexanediol<br>140 parts HX | 4 | 4 | 250 | 6 | 37.3 | 102 |
| 46 | 6 parts NPG<br>100 parts HX | 4 | 11 | 230 | 6 | 38.0 | 100 |
| 47 | 6 parts NPG<br>100 parts HX | 4 | 15 | 250 | 6 | 34.7 | 172 |
| 48 | 6 parts NPG<br>100 parts HX | 4 | 1 | 240 | 6 | 40.1 | 54 |
| 49 | 6 parts NPG<br>100 parts HX | 4 | 6 | 240 | 6 | 38.4 | 91 |
| 50 | 6 parts NPG<br>100 parts HX | 4 | 12 | 220 | 6 | 38.4 | 91 |
| 51 | 6 parts NPG<br>100 parts HX | 4 | 25 | 200 | 6 | 38.3 | 94 |
| 52 | 15 parts n-butanol<br>100 parts HX | 5<br>5 | 2<br>10 | 250<br>250 | 6<br>6 | 31.9<br>30.2 | 57<br>80 |
| 53 | 22 parts n-butanol<br>100 parts HX | 5 | 5 | 250 | 6 | 24.1 | 65 |
| 54 | 9 parts NPG<br>100 parts HX | 5<br>5 | 2<br>10 | 250<br>250 | 6<br>6 | 35.3<br>32.5 | 58<br>100 |
| 55 | 15.5 parts NPG<br>100 parts HX | 5<br>5 | 2<br>10 | 250<br>250 | 6<br>6 | 27.4<br>22.9 | 47<br>88 |
| 56 | 10 parts 2,5-hexanediol<br>100 parts HX | 5<br>5 | 2<br>10 | 250<br>250 | 6<br>6 | 33.4<br>28.6 | 91<br>140 |
| 57 | 17.6 parts 2,5-hexanediol<br>100 parts HX | 5<br>5 | 2<br>10 | 250<br>250 | 6<br>6 | 25.3<br>18.4 | 74<br>118 |
| 58 | 5.6 parts TMP<br>100 parts HX | 5<br>5 | 2<br>10 | 250<br>250 | 6<br>6 | 38.9<br>37.0 | 70<br>108 |
| 59 | 8 parts TMP<br>100 parts HX | 5<br>5 | 2<br>10 | 250<br>250 | 6<br>6 | 35.6<br>32.7 | 54<br>96 |
| 60 | 7.3 parts tripropylene glycol<br>100 parts HX | 4 | 2 | 250 | 4 | 39.4 | 70 |
| 61 | 15.9 parts<br>1000 m.w. polypropylene glycol<br>100 parts HX | 4 | 2 | 250 | 4 | 41.8 | 33 |
| 62 | 15.9 parts<br>1000 m.w. polypropylene glycol<br>100 parts HX | 4 | 4 | 250 | 4 | 41.3 | 58 |
| 63 | 7.1 parts triethyleneglycol | 4 | 4 | 250 | 4 | 40.2 | 74 |

TABLE III-continued

| Ex. | Formulation | Heat-up Time (min) | Reaction Time (min) | Reaction Temp. °C. | Cool-Down Time (min) | % NCO Reaction Mixture | % Conversion to Allophanates (Based on NCO Drops) |
|---|---|---|---|---|---|---|---|
| 64 | 100 parts HX<br>4.5 parts NPG | 4 | 8 | 250 | 4 | 31.8 | 26 |
| 65 | 100 parts IPDI<br>5.2 parts NPG | 3 | 8 | 250 | 5 | 34.0 | 80 |
| 66 | 100 parts 1,3-bis (isocyanatomethyl) cyclohexane<br>3 parts 1,3-propanediol<br>60 parts trimethylhexamethylene diisocyanate (ca. 50% 2,4,4, and 50% 2,2,4 isomers) | 3 | 4 | 250 | 5 | 28.5 | 83 |
| 67 | 5.4 parts 1,3-propanediol<br>100 parts 1,4-bis (isocyanatomethyl) cyclohexane | 3 | 4 | 250 | 5 | 30.9 | 80 |
| 68 | 6.5 parts 1,3-propanediol<br>100 parts 1,4-bis (isocyanatomethyl) cyclohexane | 3 | 4 | 250 | 5 | 29.4 | 98 |

EXAMPLE 69

To a feed tank was added a mixture of 6 parts neopentyl glycol dissolved in 100 parts hexamethylene diisocyanate. The resultant mixture had an isocyanate content of 43.3% (85% of the hydroxy groups were converted to the urethane). This material was then pumped, at 25° C., through a preheater which brought the reaction mixture to about 140° C. The mixture then entered a stirred overflow reactor purged with nitrogen and was held at 250° C. for an average residence time of 3.2 minutes. The overflow material was quench cooled to 60° C. and was found to have a 38.9% NCO content (80% conversion to allophanate based on the NCO drop). Unreacted hexamethylene diisocyanate was removed by thin layer distillation to afford a clear product with a viscosity of 5770 mPa.s/25° C. and an isocyanate content of 18.2%. The product contained 0.5% unreacted hexamethylene diisocyanate and had an APHA color of 55.

EXAMPLE 70

To a 500 ml three-necked flask equipped with a mechanical stirrer and condenser was added 100 g of hexamethylene diisocyanate. To this 34.9 g of 2-pentanol and 0.006 g of dibutyltin dilaurate were added at 25° C. with stirring. The reaction mixture while being purged with dry nitrogen was then heated over a 3.5 minute period to 250° C., held for 10 minutes, then cooled to less than 80° C. over a 5 minute period. The resulting clear liquid had an isocyanate content of 14.6%, which corresponds to an 82% conversion to allophanate based on the above NCO drop.

Although the invention has been described in detail in the foregoing for the purpose of illustration, it is to be understood that such detail is solely for that purpose and that variations can be made therein by those skilled in the art without departing from the spirit and scope of the invention except as it may be iimited by the claims.

What is claimed:

1. A process for the production of aliphatic and/or cycloaliphatic polyisocyanate containing aliphatically groups in which
   (a) an organic diisocyanate and/or polyisocyanate containing aliphatically and/or cycloaliphatically bound isocyanate groups
   is reacted with
   (b) an organic compound containing at least one hydroxyl group, which compound is otherwise inert with respect to isocyanate groups, of no more than at a temperature of at least 200° C. for a period of no more than 30 minutes to form an allophanate and the resultant product is rapidly cooled to a temperature of less than 100° C.

2. The process of claim 1 in which from 0 to 100% of the hydroxyl groups of (b) are prereacted with a portion of the isocyanate groups of (a) to form urethane groups before the allophanate-forming reaction.

3. The process of claim 1 in which the reaction mixture is cooled to a temperature of less than 100° C. within 10 minutes.

4. The process of claim 1 in which the reaction is carried out in the absence of oxygen.

5. The process of claim 1 in which the hydroxyl compound (b) is a monofunctional alcohol.

6. The process of claim 1 in which the hydroxyl groups of (b) are prereacted to form urethane groups during heat-up with the aid of a urethane catalyst.

7. The process of claim 1 in which the reaction carried out at a temperatrre of at least 250° C. for 1 to 15 minutes.

* * * * *